United States Patent [19]
Wadsworth

[11] Patent Number: 5,425,736
[45] Date of Patent: Jun. 20, 1995

[54] LIGATURE TOOL TO TENSION AND FASTEN CLIPS ON SURGICAL TUBING

[76] Inventor: LeGrand D. Wadsworth, Rte. #2 Box 68, St. Ignatius, Mont. 59865

[21] Appl. No.: 149,623

[22] Filed: Nov. 9, 1993

[51] Int. Cl.⁶ ............................................. A61B 17/00
[52] U.S. Cl. .................... 606/135; 606/140; 606/141
[58] Field of Search ............... 606/142, 151, 141, 135, 606/144, 148, 139, 167, 157; 227/901; 112/80.03, 169

[56] References Cited

U.S. PATENT DOCUMENTS

| | | | |
|---|---|---|---|
| 4,617,933 | 10/1986 | Hasson | 606/148 |
| 4,691,704 | 9/1987 | Wadsworth . | |
| 4,796,626 | 1/1989 | De Vries | 606/148 |
| 4,935,027 | 6/1990 | Yoon | 606/146 |
| 5,059,201 | 10/1991 | Asnis | 606/144 |
| 5,163,948 | 11/1992 | Kummer | 606/151 |
| 5,236,434 | 8/1993 | Callicrate | 606/141 |

Primary Examiner—Stephen C. Pellegrino
Assistant Examiner—Jeffrey A. Schmidt
Attorney, Agent, or Firm—Keith S. Bergman

[57] ABSTRACT

A ligature tool, of the type having a handle carrying an elongate body defining a fastening clip chamber in its forward part with ligature tubing holding and tensioning means carried on the body, provides improved crimping and tubing holding means. The crimping element provides a single pivotally mounted crimping dog that contacts a slit portion of an annular ligation tube clip carried in the fastening clip chamber and is movable into that chamber to crimp the sides defining the slit toward the adjacent inner surfaces of the annular clip body to fasten ligation material therebetween. The tubing holding means provide a body supporting similar laterally opposed tubing holders each having a headed vertical post about which the end portion of tubing is wound under tension before placement in an adjacent wedge-shaped slot for releasable fastening. The tubing holding body also provides tubing cutting structure.

5 Claims, 2 Drawing Sheets

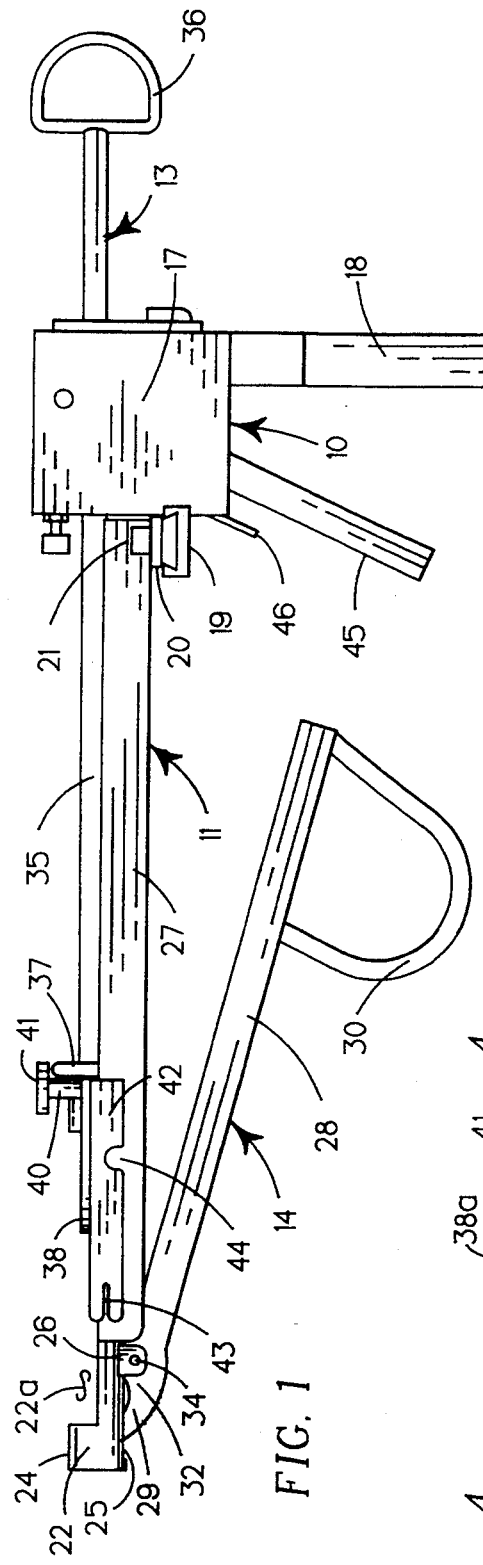

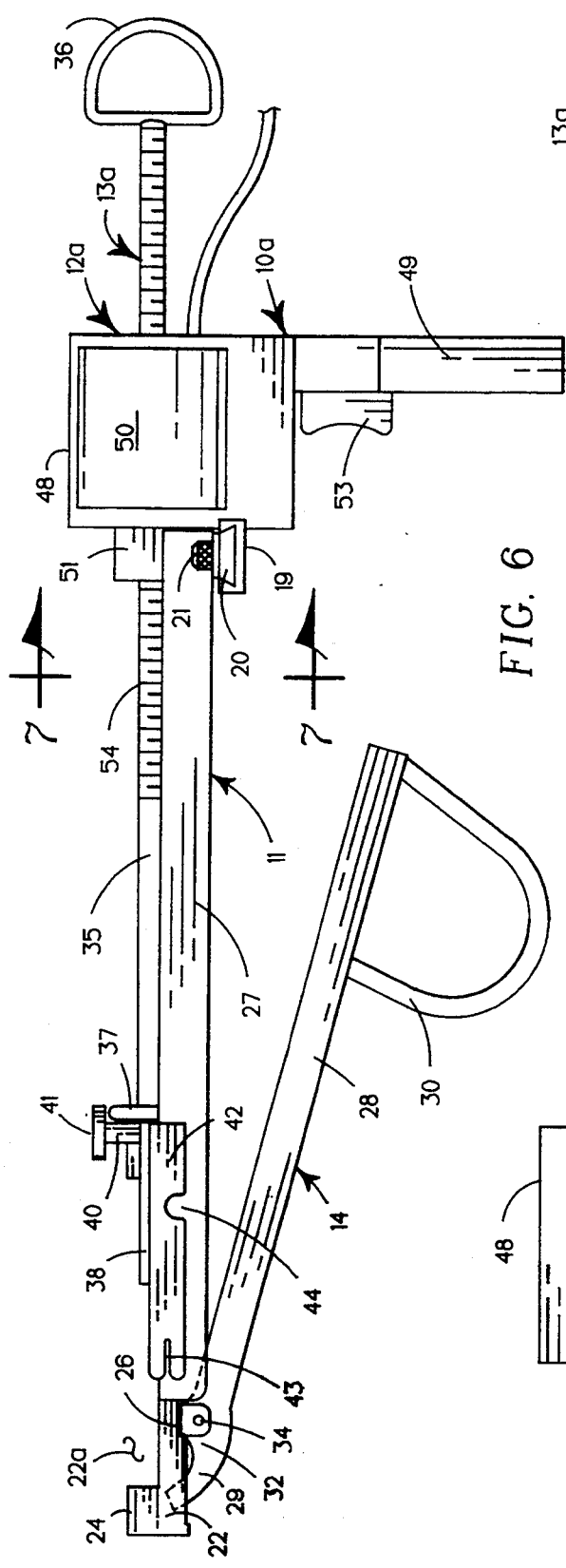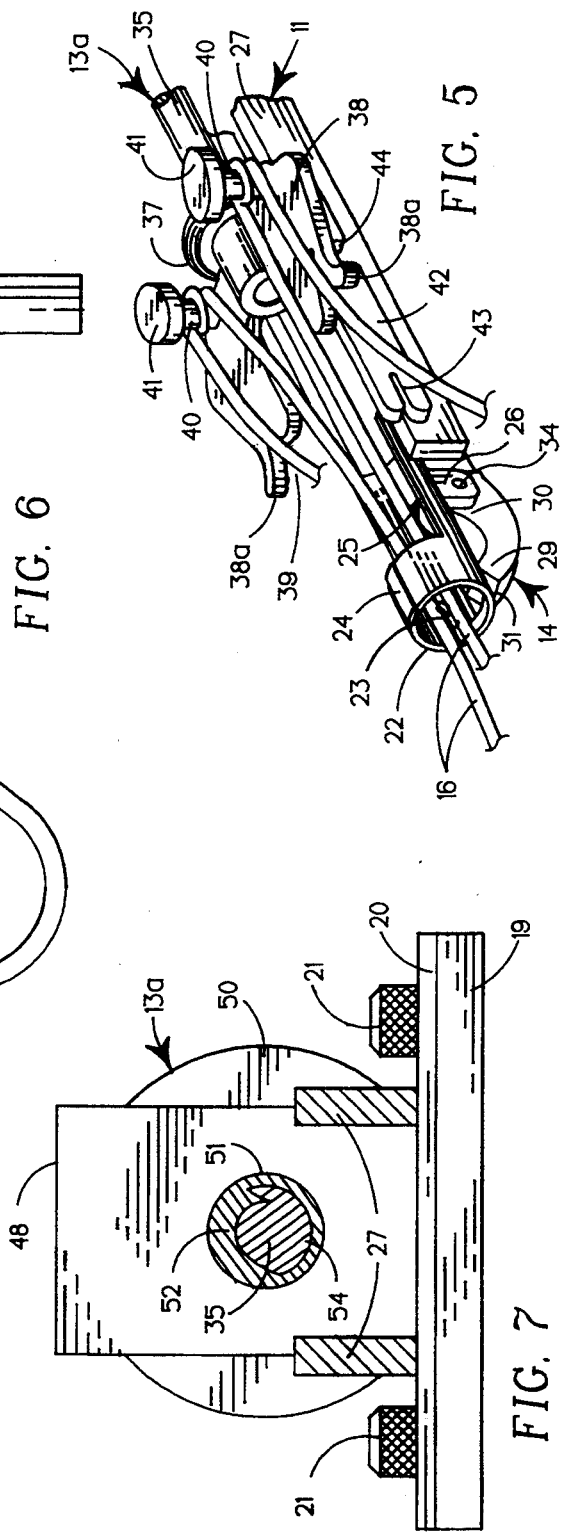

LIGATURE TOOL TO TENSION AND FASTEN CLIPS ON SURGICAL TUBING

BACKGROUND OF INVENTION

RELATED PATENTS AND APPLICATIONS

This invention is an improved ligature tool, of the type disclosed in my U.S. Pat. No. 4,691,704 and is adapted particularly for use with a split annular ligature clip of the type disclosed in my U.S. Pat. No. 5,188,637. There are no applications related hereto now filed in this or any foreign country.

FIELD OF INVENTION

This invention relates generally to ligature tools that tension and fasten elastomeric surgical tubing with split annular clips, and more particularly to such a tool that has a single pivotally operated crimping dog and post-type tubing fastening means.

BACKGROUND AND DESCRIPTION OF PRIOR ART

Ligation type castration of larger animals having external testicles carried in a scrotal pouch, especially such as bovines, has become increasingly popular in animal husbandry throughout the world. A process and tool for such purposes using elastomeric surgical tubing as a ligature and a metallic clip for fastening that tubing, was set forth in U.S. Letters Pat. No. 4,691,704 issued to the instant inventor and an improved form of split annular metallic clip for fastening such tubing was thereafter set forth in U.S. Letters Pat. No. 5,188,637 issued to the instant inventor. The instant invention provides improvements in such a tool for placement and tightening of ligation tubing fastened with such a split annular clip.

The elastomeric ligation material used witch my process and tool is common rubber surgical tubing. That tubing must be tightened so that it is under substantial tension to accomplish its purposes of ligating a body part of an animal. The forces involved, when considered in relationship to the nature of the ligation material, tend to create problems in the fastening of the ends of that material together. Some of such problems were addressed in relationship to a clip fastening each end of the tensioned ligation material in my U.S. Pat. No. 5,188,647.

The ligation material is also difficult to releasably fasten in a tool that tensions and stretches it prior to permanent fastening by some type of clip. My formerly patented tool disclosed wedge-shaped channels defined in relatively thin rigid sheet material to accomplish such temporary fastening. Experience has indicated that such fastening is not completely reliable and on occasion such tubing fasteners may sever or cause severance of the tubing rather than temporarily fastening it. My prior wedge-type fastener has also been found on occasion to allow tubing to tend to move relative to the channel in which it is fastened by reason of elastic creep and frictional motion to release some pre-established tension. This tubing movement becomes more pronounced as the angle and apex of the wedge shaped channel become larger, but if these parameters of the channel are made smaller the tendency to cut or sever the tensioned tubing increases, so with a wedge-type fastening device a compromise configuration must be used that is not completely satisfactory for holding surgical tubing without severance.

The instant releasable fastening structure resolves this problem by providing a fastener that neither severs the tensioned portion of the tubing nor allows motion of the tubing relative to the fastener. My improved fastener provides for each tubing end portion to be fastened on a headed post of curvilinear cross-section about which the tubing is wrapped, preferably by at least two turns with the outer turn overlapping the inner, before placement of the tubing in an adjacent wedge-shaped channel for releasable holding. With this structure, the higher tensioned portion of the tubing is carried on the surface of the post so that there are no edges or arcuate structures to cause or encourage severance of the tubing. The portion of the tubing that is carried in the wedge-shaped holding channel is under less tension than the portion first wrapped about the post, so that less stress is placed upon the tubing in the fastening channel. This fastening of the more relaxed portion of the tubing not only aids in preventing severance of the tubing in the fastening channel, but also aids positional maintenance of the tubing in that channel. The tubing on both sides of the channel is larger than when it was more highly stressed as in my original wedge-shaped fastener, and has greater propensity to maintain its position in the fastening channel. The overlapping of the wrapped portion of the tubing also tends to absorb more of the tension in the tubing before it is fastened in the wedge shaped channel of the fastener and also tends to better fasten the underlying tubing on the fastening post by reason of tension that exists in the overlying layer of tubing which increases the frictional engagement between the under layer of tubing and the post.

The fastening clip crimping structure of the tool disclosed in my prior patent provides two crimping dogs that pivot in opposite directions about axes parallel to the axis of the clip and are adopted particularly for crimping a unitary annular type clip such as was disclosed in that patent. That type of crimping device is operative with a split type annular clip such as disclosed in my U.S. Pat. No. 5,188,637, but it has been found that a single crimping dog that moves in a radial direction, defined by a radius extending from the clip axis to the slit, better crimps the slit type of clip.

My instant ligation tool provides such a crimping device having a single crimping dog carried by a single lever arm pivotally mounted on the tool to cause the appropriate crimping action. This type of single lever arm provides a more simple structure than a tool having two crimping arms and allows lever motion toward and away from the tool body that may be accomplished by one hand, as opposed to the radial motion of two crimping arms that required the use of two hands in my previously patented tool.

A species of my improved tool is provided with a battery operated electric motor to mechanically move the tightening bracket in either direction for tightening or loosening ligation material. In modern day animal husbandry, many bulls that are slaughtered for meat are not castrated until they are mature and brought into a feed lot for finish feeding shortly before slaughter. This practice often requires the castration of substantial numbers of mature animals, often ranging to several hundred per day, which can become an onerous task with a completely hand-operated litigation tool. The mechanized species of my tool seeks to resolve this problem.

All of these features distinguish my improved tool from known ligation castration tools for use with elastomeric tubing. My invention resides not any single feature per se, but rather in the synergistic combination of all of the improved structures of my tool that give rise to the functions necessarily flowing therefrom.

SUMMARY OF INVENTION

My improved tool for ligation castration provides a handle with an elongate body extending forwardly therefrom to define a cylindrical fastening clip chamber for positionally indexed containment of a slit annular clip to fasten portions of tensioned elastomeric ligation tubing. An elongate crimping lever defining a crimping dog at one end and a handle at the other end is pivotally mounted on the tool body, on an axis perpendicular to that of the fastening clip chamber, so that the crimping dog may be pivoted into the crimping chamber to crimp a clip carried therein. The tool handle movably carries an elongate, forwardly extending tightening member having a fastener in its forward portion to releasably fasten two end portions of ligation material. A tightening member is slidably carried on the upper portion of the tool body and extends through the handle where it engages tensioning mechanism to move it rearwardly away from the fastening clip chamber. The fastener of the tightening member provides two upwardly extending, laterally spaced, headed fastening posts, each with wedge-shaped fastening channels defined adjacent thereto, to receive tensioned elastomeric tubing for fastening by wrapping about a post and insertion in the associated fastening channel. A first species of tensioning mechanism uses the trigger operated ratchet disclosed in my prior patent to move the fastening member. A second species of tensioning mechanism provides a battery powered electric motor that selectively moves the tightening member in either a forward or rearward direction.

In creating such a tool, it is:

A principal object to provide an improved tool for ligation castration of larger animals that tensions elastomeric surgical tubing and fastens the end portions of such tensioned tubing by crimping a slit annular metallic clip thereabout.

A further object is to provide such a tool that releasably fastens litigation tubing by wrapping the tubing upon itself about a curvilinear post and thence passing it into a wedge-shaped channel so that the more highly tensioned portion of the ligation tubing is not carried in the fastening channel to avoid potentiality of severance of the tubing.

A further object is to provide such a tool that has a crimping arm defining a single crimping dog at one end and a handle at the other end, pivotally mounted for extension into a clip chamber to crimp a slit annular clip in a radial direction at the slit portion.

A further object is to provide such a tool that has a fastening member that in first species may be operated manually or in a second species may be operated by a battery powered electric motor.

A still further object is to provide such a tool that is of new and novel design, of rugged and durable nature, of simple and economic manufacture and operation and is otherwise well suited to the uses and purposes for which it is intended.

Other and further objects of my invention will appear from the following specification and accompanying drawings which form a part hereof. In carrying out the objects of my invention, however, it is to be understood that its essential features are susceptible of change in design and structural arrangement with only one preferred and practical embodiment being illustrated in the accompanying drawings as is required.

BRIEF DESCRIPTION OF DRAWINGS

In the accompanying drawings which form a part hereof and wherein like numbers of reference refer to similar parts throughout:

FIG. 1 is an orthographic side elevational view of a first species of my improved tool showing its various parts, their configuration and relationship.

FIG. 2 is an orthographic top view of the tool of FIG. 1.

FIG. 3 is an enlarged top view of the handle showing the operative mechanism carried therein in more detail.

FIG. 4 is a partial elongate vertical cross-sectional view through the clip chamber of the tool of FIG. 2 taken on the line 4—4 in the direction indicated by the arrows.

FIG. 5 is an isometric view of the forward portion of the body and the fastening member, showing the fastening of elastomeric ligation tubing.

FIG. 6 is an orthographic side elevational view of a second species of my tool having a motor powered fastening member.

FIG. 7 is a somewhat enlarged transverse vertical cross-sectional view through the tool of FIG. 6, taken on the line 7—7 thereon in the direction indicated by the arrows, to show one type of interconnection of a motor with the fastening arm.

DESCRIPTION OF THE PREFERRED EMBODIMENT

My invention generally provides handle 10 supporting forwardly extending elongate body 11 defining a forward clip chamber carrying clip 15 to fasten two adjacent portions of ligation tubing 16. The handle carries tensioning mechanism 12 which selectively moves tensioning member 13 a forward and rearward direction and the body carries crimping member 14.

Handle 10 provides body 17 peripherally formed to define an internal chamber to carry operative mechanism that supports and moves tensioning member 13, The handle body structurally supports depending handle element 18 to aid manual manipulation and forwardly extending body bracket 19 defining in its upper surface a laterally extending channel to fastenably receive a body bracket.

Body 11 comprises two spacedly adjacent elongate beams 27 structurally carrying in their rearward portions fastening bracket 20 communicating therebetween and configured for a conformable fit in the channel defined in body bracket 19, Plural bolts 21 threadedly engage in cooperating holes defined in the brackets 19, 20 to extend therebetween to releasably fasten and positionally maintain those brackets relative to each other.

The forward portions of beams 27 carry tubular crimping cylinder 22 extending spacedly forwardly therebetween, The crimping cylinder 22 defines clip chamber 23 in its forward portion to receive a clip 15 and in its upper forward periphery the cylinder defines indexing channel 24 communicating with the clip chamber and extending spacedly rearwardly from the forward surface of the crimping cylinder. The upper rearward portion 22a of the crimping cylinder is removed to aid manual manipulation of tubing and the lower medial portion defines crimping dog slot 25. Spaced depending crimping arm ears 26, structurally carried laterally adjacent the rearward portion of each side of crimping dog slot 25, each define cooperating aligned pivot pin holes to receive pivot pin 34 therebetween.

Crimping member 14 provides elongate lever body 28 defining crimping dog 29 in its forward end portion and handle 30 depending from its lower rearward end portion. The crimping dog 29 has an upwardly and forwardly curving configuration, as illustrated, with an uppermost linear edge 31 configured to crimp a split-type clip 15. The upper rearward portion 32 of the crimping dog defines a pivot pin hole to receive pivot pin 34 extending between crimping arm ears 26 and through the crimping dog. The length of body lever 28 is limited so that the crimping member may pivot to a position with the upper portion of the lever body substantially parallel with the lower surface of body beams 27 without the rearward portion of the crimping member interfering with the handle structure or trigger mechanism. The width of the crimping dog should be approximately one-third of the diameter of the crimping chamber and the edge 31 should be pivotal upwardly to a point spacedly above the axis of the clip chamber 23 to properly crimp a split clip of the type disclosed in my prior patent.

Tensioning member 13 provides elongate body rod 35 extending from the forward portion of body beams 27 rearwardly through handle structure 10 and a spaced distance rearwardly therebeyond to there carry "D" shaped loop 36 in its rearward end portion to aid manual manipulation. The forward portion of the body rod 35 is carried in annular fastening collar 37 which in turn structurally carries horizontal fastening plate 38. Fastening plate 38 is a planar element, somewhat wider than the distance between body beams 27, so that the plate extends laterally past both body beams for sliding support thereon. The plate 38 extends spacedly forwardly of body rod 35 to the rearward portion of crimping cylinder 22. Each forward lateral portion of the fastening plate 38 defines a rearwardly tapering channel 39 to fasten ligation tubing therein. The channels 39 preferably do not taper to a sharp point but rather have some width and are rounded in their rearward apex to aid in preventing severance of tubing held therein. The portion 38a of the plate 38 defining the laterally outer forward portion of channel 39 preferably curves laterally outwardly in a forward direction to aid placement of tubing in the channel.

The rearward portions of the fastening plate 38 laterally of each side of fastening collar 37 structurally carry upstanding fastening posts 40, each having head 41 in its upper portion. The vertical height of fastening posts 40 is at least as great as the diameter of ligation tubing 16 to be fastened thereon, and the edges and surfaces of both the fastening posts and their heads are of a rounded curvilinear nature so as to present no sharp, acute or irregular surfaces or edges that might aid or promote the tearing or severance of tensioned ligation tubing fastened thereon.

Fastening plate 38 carries trimmer plate 42 structurally depending therefrom spacedly laterally of the outer surface of a body beam on one side. The trimmer plate 42 extends forward, of the fastening plate to define channel 43 in which ligation tubing may be positioned for measured cutting or by which it may be cut if desired. The medial lower portion of the trimmer plate defines tubing notch 44 to allow passage of tubing for passage between the trimmer plate and adjacent body beam.

Tensioning mechanism 12 carried by the handle 10 provides means for moving tensioning member 13 in a forward-rearward direction to tighten or loosen a loop of elastomeric ligation tubing carried in the tool. The first species of tensioning mechanism shown in FIG. 1 is the type disclosed in my prior U.S. Pat. No. 4,691,704. With this type of tensioning mechanism, handle trigger 45 may be grasped by the fingers of a user and moved toward handle element 18 to cause tensioning member 13 to move incrementally rearwardly responsive to each rearward motion of the trigger 45. The tensioning member may be released from interconnection with the tensioning mechanism by motion of release lever 46 so that the tensioning member may be freely manually moved in a forward direction. The tensioning member may be freely moved in a rearward direction by manually moving the tensioning rod 35 rearwardly by manipulation of the "D" shaped loop 36. As long as the tensioning member is interconnected with the tensioning mechanism, positioning of the tensioning member will be maintained against forward displacement. This type of structure in essence is known, such as in caulking guns, and is quite effective for use in my tool when the tool is manually operated as set forth in detail my aforesaid patent.

A second species of tensioning mechanism providing a battery powered electric motor is shown in FIGS. 6 and 7. This species provides the same body structure 11, crimping structure 14 and forward portion of fastening structure 13a, but has a modified fastening rod body and handle structure 10a to provide mechanized operation of the tensioning member. The second species in essence embodies the improved crimping and tubing fastening structure of the first species, but additionally adds mechanical means for tensioning ligation tubing.

As seen in FIGS. 6 and 7, the second species provides modified tensioning mechanism 12a providing handle body 48, with depending handle element 49. The handle body carries electrically powered motor 50 having hollow drive shaft 51. The internal surface of the drive shaft 51 defines threads 52 to operatively receive complementary external threads 54 defined in the rearward portion of tensioning rod 35. Motor 50 is powered by an external electrical source (not shown), preferably a battery pack that is separate from, the tool itself, though battery powering sources carried in or on the tool and alternating current sources are within the scope of my invention for powering motor 50.

Handle element 49 carries two pole, double throw switch 53. This switch in neutral position, without either end depressed, cuts off power to motor 50 to render the motor inoperative and causes the motor to rotate in opposite directions by depression of the opposite ends of the switch. Such an electric motor is well known, available as an ordinary item of commerce in the present day market place, and therefore not specified or illustrated in detail.

The tensioning member 13a of the second species differs from that element in the first species by providing external threads 54 in the rearward portion of tensioning rod 35. These external threads are configured to be mattingly received by internal threads 52 defined in the medial channel of drive shaft 51 of motor 50 so that when the two elements are threadedly engaged, as illustrated in FIG. 6, the tensioning rod 35 will be moved forwardly or rearwardly responsive to rotary motion of drive shaft 51.

Various other methods of interconnecting the tensioning rod with the rotating shaft of a motor to cause linear motion of the tensioning rod are known and those other methods are within the scope of my invention.

Having thusly described the structure of by improved ligation tool, its operation may be understood.

Both the instant tool and the slit clips used in it operate in the same essential fashion as described in my prior patents on those devices. As seen in FIG. 5, a loop is formed in a length of surgical tubing 16 and the two end portions are passed rearwardly through split clip 15 carried in clip chamber 22. The ends of the tubing are manually moved rearwardly until they are spacedly rearward of fastening posts 40. One tube end is then wound about one fastening post, preferably with two turns of tubing with the second turn at least partially overlapping the first, as illustrated, and the end portion of the tubing is then moved forwardly and inserted with some tension and deformation in slot 39, where when released it will be held by reason of the lack of tension and consequent larger diameter of the untensioned end portion of the tubing and its deformation. The second tube is then similarly placed on the other fastening post and in the other slot associated therewith. The loop of tubing forwardly of the clip is then placed about the scrotal pouch of an animal, if this already has not been accomplished, and the tool is ready for tensioning of the loop.

Tensioning in the case of the manually operated tool is accomplished by moving trigger 45 toward handle 18 repeatedly until the tube has been appropriately tensioned. In the case of the motorized species of my tool, switch 53 is depressed at the proper end to operate the motor to move tensioning rod 35 in a rearward direction until sufficient tensioning in the surgical tubing has been accomplished.

To fasten the tubing after tensioning has been accomplished, handle 30 of crimping arm 28 is manually grasped and moved by the user away from the tool body to move edge 31 of the crimping dog inwardly into clip chamber 23. As this motion is accomplished, both sides of annular clip 15 adjacent the slit defined therein will be contacted by edge 31 and moved inwardly toward the opposite side of the clip to fasten ligation tubing in each side portion of the clip as described in my patent upon a slit clip. When the crimping of the clip is complete and the two tubing ends are fastened therein, the crimping member handle 30 is moved toward the tool body to release engagement of the crimping dog with the clip so that the tool may be removed therefrom.

If it is desired to trim the tubing ends in the tool, the tubing may be removed from slots 39, unwrapped from posts 40 and placed in cutting channel 43 where it may be severed by manually moving it rearwardly in the slot. More commonly, however, the material will be cut by some other cutting tool rearwardly of the clip and forwardly of fastening post 40 to provide relatively short neatly trimmed tubing ends. If a user is working with a longer length of ligation tubing suitable for multiple ligations and desires that the longer portion of that tubing be severed, especially as before tensioning of the tubing and fastening a clip thereon, the longer end of that tubing may be inserted in slot 43 of cutter member 42 and severed therein so that the reserve tubing may be removed from any connection with my tool for convenience.

The foregoing description of my invention is necessarily of a detailed nature so that a specific embodiment of its best mode might be set forth as required, but it is to be understood that various modifications of detail, rearrangement and multiplication of parts might be resorted to without departing from its spirit, essence or scope.

Having thusly described my invention, what I desire to protect by Letters Patent, and

What I claim is:

1. In a ligation tool to tension and fasten elastomeric tubing about a ligation site, of the type having a handle carrying an elongate forwardly extending body defining a fastening clip chamber in its forward portion with a tubing tensioning member supported by the body and a tensioning mechanism to move the tensioning member rearwardly toward the handle, the improvements comprising, in combination:

a crimping member pivotally carried by the body and having a crimping dog defined in its forward portion to extend into the fastening clip chamber responsive to pivotal motion of the crimping member to crimp a clip carried in the crimping chamber to fasten two portions of ligation tubing extending through the clip, and means for releasably fastening tubing defined by the tensioning member which comprises two laterally spaced, vertical fastening posts and two adjacent, wedge-shaped fastening channels, each channel defined in the tensioning member adjacent to but spaced from one of said fastening posts, with the apex of said wedge-shaped channel facing the associated fastening post so that. ligation tubing may be wrapped around a fastening post and an end portion of the tubing releasably fastened in the associated wedge-shaped channel.

2. The improvements of claim 1 further including tubing cutting means comprising a trimmer plate carried by the tensioning member laterally of the body and defining a wedge-shaped cutting channel in which tubing may be positioned and severed.

3. The improvements of claim 1 wherein the tensioning member is operatively connected with the tensioning mechanism which comprises an electric motor carried in the handle, for selective motion of said tensioning member toward and away from the motor responsive to rotation of said motor to tighten and loosen ligation tubing carried by the tensioning member.

4. A ligature tool to tension a loop of elastomeric tubing about a ligation site and fasten the ends of the tubing by crimping a slit annular clip about the adjacent portions of the tubing immediately adjacent the ligation loop for the castration of large animals, comprising in combination:

handle supporting an elongate forwardly extending body defining a fastening clip chamber in its forward end portion; a tensioning member carried by the handle to extend therethrough, said tensioning member carrying tubing holding means in its forward portion for sliding support on the elongate body, said tubing holding means having a flat body supporting two laterally spaced upwardly extending fastening posts having enlarged uppermost heads, said flat body defining wedge-shaped tubing fastening channels adjacent each fastening post with the apex of each channel facing toward the associated fastening post, said. fastening channels configured to receive and releasably hold elastomeric tubing;

a tensioning mechanism carried by the handle and operatively communicating with the tensioning member to move the tensioning member rearwardly from the clip chamber to tension tubing extending through the clip chamber; and an elongate crimping element defining a forward crimping dog curving forwardly and upwardly to form an upper edge with a width not greater than approximately one-half of the diameter of the clip to be crimped, said crimping element being pivotally mounted on the body spacedly rearwardly adjacent of the fastening clip chamber to extend parallel to the body so that the crimping dog is pivotally movable into the fastening clip chamber to crimp a slit clip carried therein.

5. The tool of claim 4 wherein the tensioning mechanism includes an electric motor carried in the handle to operatively communicate with the tensioning member for selective forward and rearward motion responsive to rotation of said motor.

* * * * *